United States Patent [19]

Young et al.

[11] Patent Number: 5,633,169
[45] Date of Patent: May 27, 1997

[54] MEASUREMENT OF CARBON DIOXIDE IN BLOOD

[75] Inventors: Chung C. Young, Weston; Jeffrey Chien, Ashland, both of Mass.

[73] Assignee: Nova Biomedical Corporation, Waltham, Mass.

[21] Appl. No.: 549,028

[22] Filed: Oct. 27, 1995

[51] Int. Cl.[6] ............................... G01N 33/50
[52] U.S. Cl. .............. 436/68; 436/70; 436/163; 436/179
[58] Field of Search .................... 436/11, 68, 70, 436/133, 163, 179, 181; 422/73, 82.02

[56] References Cited

U.S. PATENT DOCUMENTS

| | | | |
|---|---|---|---|
| H602 | 3/1989 | Terashima | 436/18 |
| 3,763,422 | 10/1973 | MacPhee et al. | 324/438 |
| 3,973,912 | 8/1976 | Trafton et al. | 436/68 |
| 4,001,142 | 1/1977 | Turner | 436/11 |
| 4,003,705 | 1/1977 | Buzza et al. | 436/68 |
| 4,151,108 | 4/1979 | Sorensen et al. | 436/11 |
| 4,299,728 | 11/1981 | Cormier et al. | 436/11 |
| 4,321,545 | 3/1982 | Cameron | 324/442 |
| 4,369,127 | 1/1983 | Cormier et al. | 436/11 |
| 4,686,479 | 8/1987 | Young et al. | 205/781.5 |
| 4,757,002 | 7/1988 | Joo | 435/7.92 |
| 4,871,439 | 10/1989 | Enzer et al. | 204/401 |
| 5,429,930 | 7/1995 | Cunningham et al. | 435/15 |

*Primary Examiner*—Jill Warden
*Assistant Examiner*—Maureen M. Wallenhorst
*Attorney, Agent, or Firm*—Fish & Richardson P.C.

[57] ABSTRACT

A method of determining the total carbon dioxide concentration in plasma ($TCO_{2\ plasma}$) directly from a whole blood sample involves adjusting total carbon dioxide concentration measured in the whole blood sample ($TCO_{2\ whole\ blood}$) using a volume dilution factor (VDF) to give a value that is equivalent to $TCO_{2\ plasma}$.

8 Claims, 1 Drawing Sheet

MEASUREMENT OF CARBON DIOXIDE IN BLOOD

The invention relates to the determination of the total carbon dioxide concentration in a whole blood sample.

BACKGROUND OF THE INVENTION

The measurement of total carbon dioxide concentration. ($TCO_2$) in serum or plasma is a routine analysis performed in clinical laboratories as a patient profile test. In particular, measurement of $TCO_2$ is useful in determining the acid-base status of a patient. For example, plasma $TCO_2$ can be used by a physician in the diagnosis of a patient in renal failure or acute acidosis.

$TCO_2$ in serum or plasma is comprised of three major chemical forms: dissolved $CO_2$ (3%); carbamino (R—$NHCOO^-$) derivatives of plasma protein (33%); and bicarbonate ($HCO_3^-$) anion (64%). Other minor forms include carbonic acid ($H_2CO_3$) and carbonate anion ($CO_3^=$).

Most of the procedures that quantify $TCO_2$ in serum or plasma involve acidification of the sample to convert all of the $CO_2$-containing species to $CO_2$ gas, as is summarized in equation (1):

$$CO_2 + R-NHCOO^- + HCO_3^- + H_2CO_3 + \quad (1)$$

$$CO_3^= + Acid \longrightarrow CO_2 \uparrow + H_2O$$

Once liberated, the $CO_2$ gas can be measured manometrically in batch analysis or by continuous-flow procedures where the $CO_2$ gas diffuses across a membrane into a bicarbonate-containing solution thereby lowering the pH of the solution. The change in pH can be detected either potentiometrically using a pH glass electrode or spectrophotometrically if the bicarbonate buffer contains a pH indicating dye. Additionally, there are detection methods that use enzymes or bicarbonate-selective electrodes to quantify $TCO_2$. These techniques apply to serum or plasma samples. Therefore, centrifugation of the whole blood sample to separate the cells and plasma prior to analysis is required.

SUMMARY OF THE INVENTION

The invention relates to the determination of $TCO_2$ in plasma or serum directly from a whole blood sample. The $TCO_2$ in plasma is essentially equivalent to the $TCO_2$ in serum; $TCO_2$ plasma will be used herein to denote either value. The method involves adjusting $TCO_2$ measured in the whole blood sample ($TCO_{2\ whole\ blood}$) using a volume dilution factor (VDF) to provide $TCO_{2\ plasma}$. The VDF is determined for each whole blood sample and, preferably, can be related directly to the hematocrit (Hct) of that sample.

An advantage of the present invention is that $TCO_{2\ plasma}$ can be determined accurately and directly from a whole blood sample. Since the measurement does not depend on plasma or serum samples, the method of the invention avoids time-consuming sample preparation steps.

Other features and advantages of the invention will be apparent from the description of the preferred embodiment thereof, and from the claims.

BRIEF DESCRIPTION OF THE DRAWING

The FIGURE is a fluid flow diagram of the blood chemistry analyzer used to determine $TCO_2$ plasma.

DESCRIPTION OF THE PREFERRED EMBODIMENTS

Figure 1:
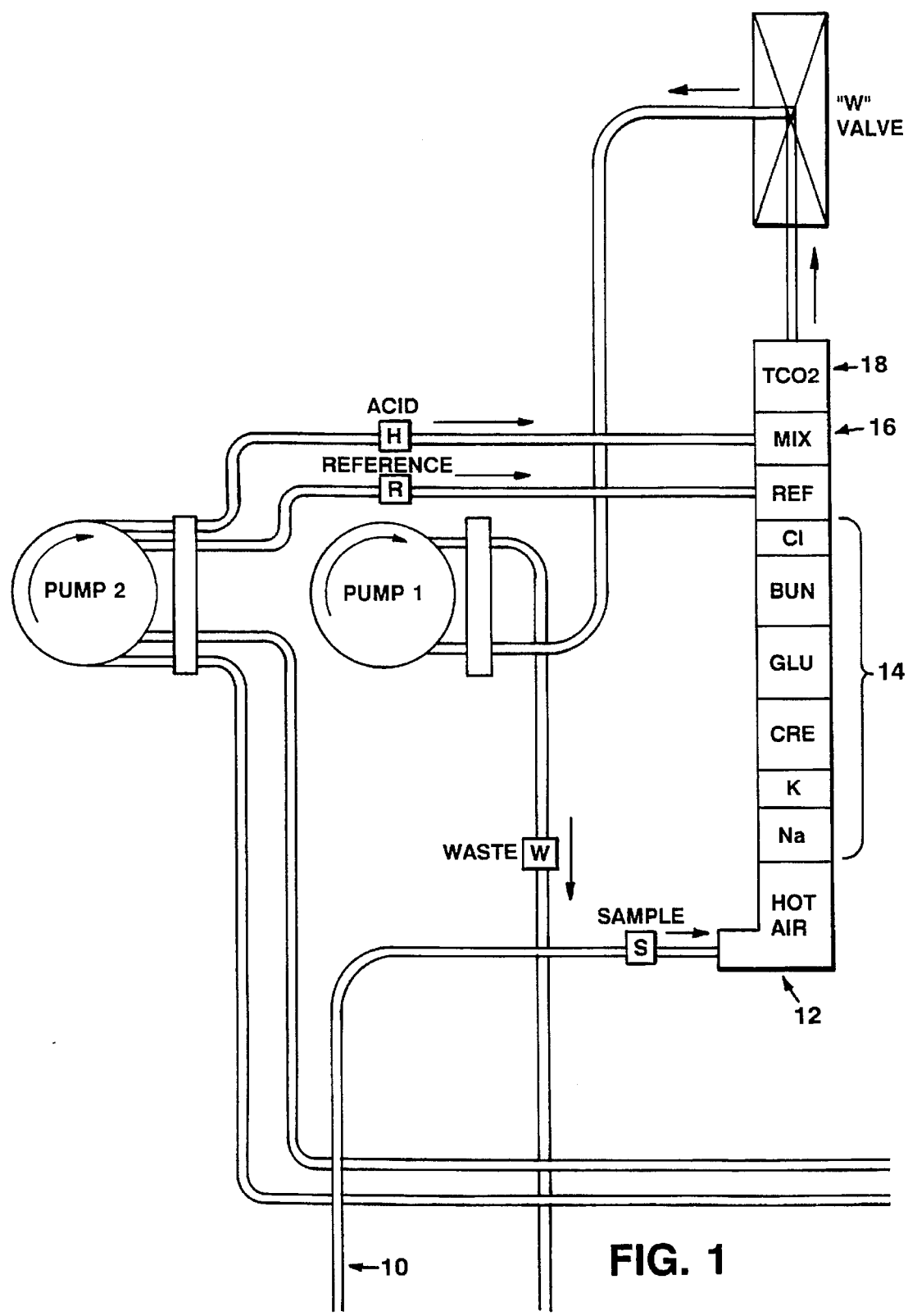

The preferred method includes measuring $TCO_{2\ whole\ blood}$ in a whole blood sample, generating a VDF from the Hct of the same whole blood sample, and adjusting the $TCO_{2\ whole\ blood}$ using the VDF to provide the $TCO_{2\ plasma}$ of the whole blood sample.

Methods for measuring $TCO_2$ are described in U.S. Pat. Nos. 3,973,912, 4,321,545 and 5,429,930, each of which is incorporated by reference. The preferred method of measuring $TCO_{2\ whole\ blood}$ involves acidification of the whole blood sample to liberate $CO_2$ gas from the sample according to equation (1). The sample and acidifying agent mix as they pass through a mixing chamber. Acidifying agents include aqueous solutions of sulfuric acid, citric acid, lactic acid and combinations thereof. The preferred acidifying agent is an aqueous solution containing 90 mM citric acid, although the concentration can be varied over a wide range.

The preferred $TCO_2$ gas electrode includes a pH glass electrode along with a Ag/AgCl reference electrode. The two electrodes are covered by a $CO_2$ gas permeable membrane such as silicone membrane. A bicarbonate/chloride internal filling solution (IFS) is trapped between the membrane and the pH electrode. The $CO_2$ gas generated by acidification passes through the silicone membrane. It equilibrates with the IFS. The pH of the IFS will change with the $CO_2$ concentration. By measuring pH with the pH glass electrode, the $CO_2$ concentration can be determined.

The $TCO_2$ gas electrode is calibrated before use. Calibration involves using two standard aqueous bicarbonate solutions. Each standard solution, when mixed with acid, will produce a known $CO_2$ concentration which in turn will produce a known pH in the IFS trapped between the membrane and the pH electrode. Once the $TCO_2$ electrode is calibrated, $TCO_2$ whole blood is determined comparing the unknown with one calibration standard.

$TCO_{2\ plasma}$ is obtained by adjusting the measured $TCO_{2\ whole\ blood}$ using the VDF of the same sample. The preferred adjustment is shown in equation (2):

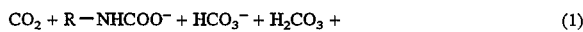

$$TCO_{2\ plasma} = TCO_{2\ whole\ blood}/VDF \quad (2)$$

The VDF represents the fractional volume of the extracellular fluid in the whole blood sample. Preferably, the VDF is determined from the Hct of the same whole blood sample according to equation (3):

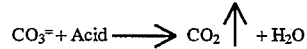

$$VDF = 1 - Hct/100 \quad (3)$$

Hct is the volume of red blood cells occupying the total volume of the whole blood sample reported as a percentage. Hct measurement is performed routinely in clinical laboratories using various methods to diagnose conditions such as anemia or polycythemia. The preferred method of determining Hct is by measuring the conductivity of the whole blood sample using a pair of calibrated electrodes as disclosed in U.S. Pat. No. 4,686,479. The Hct sensor may be factory calibrated or calibrated using aqueous standards.

$TCO_{2\ plasma}$ obtained from analyzing a whole blood sample following the method of the invention is equivalent to the $TCO_2$ determined after isolating the plasma from the whole blood sample by centrifugation. Table I lists $TCO_2$ data of patients that was measured in whole blood and in the separated plasma. The plasma samples acquired from the corresponding blood samples were subsequently analyzed under identical conditions to obtain the directly measured $TCO_{2\ plasma}$. Hct of the whole blood sample was measured by the method disclosed in U.S. Pat. No. 4,686,479. Finally, the $TCO_{2\ whole\ blood}$ was adjusted according to equations (2) and (3). The data in Table I indicate that $TCO_{2\ plasma}$ measured using the preferred method correlates with $TCO_{2\ plasma}$ measured directly in plasma samples.

TABLE I

| Patient ID | Measured $TCO_{2\ blood}$ (mmol/L) | Hct (%) | $TCO_{2\ blood}$ [1-Hct/100] (mmol/L) | Measured $TCO_{2\ plasma}$ (mmol/L) |
|---|---|---|---|---|
| 1 | 15 | 45 | 27 | 27 |
| 2 | 16 | 38 | 26 | 25 |
| 3 | 16 | 41 | 27 | 27 |
| 4 | 16 | 39 | 26 | 24 |
| 5 | 16 | 41 | 27 | 24 |
| 6 | 14 | 44 | 25 | 27 |
| 7 | 14 | 42 | 24 | 25 |
| 8 | 15 | 45 | 27 | 25 |
| 9 | 19 | 38 | 31 | 30 |
| 10 | 14 | 45 | 25 | 25 |
| 11 | 13 | 52 | 27 | 26 |
| 12 | 12 | 42 | 21 | 22 |
| 13 | 16 | 38 | 26 | 25 |
| 14 | 16 | 39 | 26 | 23 |
| 15 | 14 | 44 | 25 | 27 |
| 16 | 13 | 45 | 24 | 22 |
| 17 | 15 | 43 | 26 | 28 |
| 18 | 16 | 41 | 27 | 26 |
| 19 | 15 | 43 | 26 | 28 |
| 20 | 16 | 41 | 27 | 31 |
| 21 | 8 | 43 | 14 | 13 |
| 22 | 16 | 41 | 27 | 26 |
| 23 | 29 | 37 | 46 | 47 |
| 24 | 11 | 43 | 19 | 17 |
| 25 | 27 | 37 | 43 | 44 |
| 26 | 7 | 40 | 12 | 11 |
| 27 | 26 | 37 | 41 | 42 |
| 28 | 9 | 42 | 16 | 14 |
| 29 | 15 | 44 | 27 | 29 |
| 30 | 15 | 42 | 26 | 26 |

The method of the invention can be used in most typical blood chemistry analyzers. The features of a preferred blood chemistry analyzer are presented in the figure, which shows the preferred arrangement of pumps and analysis chambers in the analyzer. The analyzer includes two peristaltic pumps and a series of analysis chambers. Pump 1 draws the sample through tube 10 into analysis chamber 12 where the Hct of the sample is determined if the sample is a whole blood sample. The sample then flows through a set of analysis chambers 14 where other sample chemistry is probed. The sample and acidifying agent are then combined in mixing chamber 16. The acidifying agent is delivered to chamber 16 by pump 2. The mixture flows to chamber 18 which houses a $TCO_2$ gas electrode. The liberated $CO_2$ gas is measured in chamber 18 using a $TCO_2$ gas electrode, and related to $TCO_2$ in the sample. The $TCO_2$ in the whole blood sample is then converted to $TCO_{2\ plasma}$ using the data collected for that sample.

The $TCO_{2\ plasma}$ measurement described above can be incorporated into a NOVA CRT12 or CRT14 Chemistry Analyzer, which is available from Nova Biomedical Corp., with appropriate modification. The analyzer allows most of the blood chemistry to be determined in a single run of a whole blood sample, decreasing sample analysis time which is critical in emergency situations.

Other embodiments are within the claims.

What is claimed is:

1. A method of determining the total $CO_2$ concentration in plasma of a whole blood sample, said whole blood sample containing red blood cells and plasma, wherein the fractional volume of said plasma in said whole blood sample comprises a volume dilution factor of said whole blood sample, said method comprising:

(a) loading an uncentrifuged whole blood sample containing red blood cells and plasma into a blood chemistry analyzer including a $CO_2$ sensor and a hematocrit-measuring station;

(b) measuring the total $CO_2$ concentration of said uncentrifuged whole blood sample containing red blood cells and plasma with said $CO_2$ sensor;

(c) measuring the hematocrit of said uncentrifuged whole blood sample containing red blood cells and plasma at said hematocrit-measuring station;

(d) generating the volume dilution factor of said uncentrifuged whole blood sample containing red blood cells and plasma from said hematocrit; and (e) adjusting the total $CO_2$ concentration of said uncentrifuged whole blood sample containing red blood cells and plasma using said volume dilution factor to provide the total $CO_2$ concentration in plasma of said uncentrifuged whole blood sample.

2. The method of claim 1, wherein the total $CO_2$ concentration of the uncentrifuged whole blood sample is determined by the addition of an acidifying agent to said uncentrifuged whole blood sample to liberate $CO_2$ gas which is quantified by a detector.

3. The method of claim 2, wherein the acidifying agent is an aqueous solution comprised of an acid more acidic than carbonic acid.

4. The method of claim 3, wherein the acid is citric acid.

5. The method of claim 2, wherein the acidifying agent is an aqueous solution containing sulfuric acid.

6. The method of claim 2, wherein the detector of liberated $CO_2$ gas is a manometer.

7. The method of claim 2, wherein the detector of liberated $CO_2$ gas is a pH glass electrode.

8. The method of claim 1, wherein hematocrit is determined by impedance or conductance.

* * * * *